(12) United States Patent
Barnes et al.

(10) Patent No.: US 7,095,018 B2
(45) Date of Patent: Aug. 22, 2006

(54) DEPOSITION OF SAMPLES AND SAMPLE MATRIX FOR ENHANCING THE SENSITIVITY OF MATRIX ASSISTED LASER DESORPTION/IONIZATION MASS SPECTROMETRY

(75) Inventors: David M. Barnes, Fort Atkinson, WI (US); Bradley J. Larson, Madison, WI (US); Max G. Lagally, Madison, WI (US); Martha M. Vestling, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/025,349

(22) Filed: Dec. 29, 2004

(65) Prior Publication Data

US 2006/0138319 A1 Jun. 29, 2006

(51) Int. Cl.
*H01J 49/00* (2006.01)
*C12Q 1/68* (2006.01)

(52) U.S. Cl. .................. 250/288; 250/281; 250/282; 239/86

(58) Field of Classification Search ............... 250/281, 250/282, 285, 288
See application file for complete search history.

(56) References Cited

U.S. PATENT DOCUMENTS

| | | | |
|---|---|---|---|
| 4,334,531 A * | 6/1982 | Reichl et al. ........ | 128/200.14 |
| 5,808,300 A | 9/1998 | Caprioli | |
| 6,175,112 B1 | 1/2001 | Karger et al. | |
| 6,232,129 B1 | 5/2001 | Wiktor | |
| 6,287,872 B1 | 9/2001 | Schurenberg et al. | |
| 6,508,986 B1 | 1/2003 | Anderson et al. | |
| 6,569,385 B1 | 5/2003 | Little et al. | |
| 6,603,118 B1 | 8/2003 | Ellson et al. | |
| 6,612,686 B1 | 9/2003 | Mutz et al. | |
| 6,710,335 B1 | 3/2004 | Ellson et al. | |
| 6,753,521 B1 | 6/2004 | Park et al. | |
| 6,781,122 B1 | 8/2004 | Colburn et al. | |
| 6,874,699 B1 * | 4/2005 | Larson et al. ........ | 239/102.1 |
| 2004/0071601 A1 | 4/2004 | Larson et al. | |
| 2005/0116161 A1 * | 6/2005 | Hafeman et al. ........ | 250/282 |
| 2005/0153344 A1 * | 7/2005 | Diamond et al. ........ | 435/6 |
| 2005/0156056 A1 * | 7/2005 | Larson et al. ........ | 239/102.1 |
| 2005/0196791 A1 * | 9/2005 | Koopman et al. ........ | 435/6 |
| 2006/0016984 A1 * | 1/2006 | Finch et al. ........ | 250/288 |
| 2006/0040334 A1 * | 2/2006 | Thompson ........ | 435/23 |

OTHER PUBLICATIONS

Lin He, et al., "337 nm Matrix-Assisted Laser Desorption/Ionization of Single Aerosol Particles," J. Mass Spectrom., vol. 34, 1999, pp. 909-914.

Torbjorn Johnson, et al., "A CE-MALDI Interface Based on the Use of Prestructured Sample Supports," Analytical Chemistry, vol. 73, No. 8, Apr. 15, 2001, pp. 1670-1675.

Sabina Santesson, et al., "Airborne Cell Analysis," Analytical Chemistry, vol. 72, No. 15, Aug. 1, 2000, pp. 3412-3418.

(Continued)

*Primary Examiner*—Nikita Wells
*Assistant Examiner*—Bernard E. Souw
(74) *Attorney, Agent, or Firm*—Foley & Lardner LLP

(57) ABSTRACT

The present invention relates to small sample spots for MALDI targets and methods for producing the same. The sample spots are composed of a layer of matrix material and a layer of analyte. In some instances, the samples spots have diameters of no more than 50 micrometers or even smaller. The sample spots are deposited onto a MALDI target substrate using ultrasonic deposition from a nozzle.

20 Claims, 6 Drawing Sheets

OTHER PUBLICATIONS

Christer Ericson, et al., "An Automated Noncontact Deposition Interface for Liquid Chromatography Matrix-Assisted Laser Desorption/Ionization Mass Spectrometry," Analytical Chemistry, vol. 75, No. 10, May 15, 2003, pp. 2309-2315.

Michael A.R. Meier, et al., "Automated Multiple-Layer Spotting for Matrix-Assisted Laser Desorption/Ionization Time-of-Flight Mass Spectrometry of Synthetic Polymers Utilizing Ink-Jet Printing Technology," Rapid Communications in Mass Spectrometry, vol. 17, 2003, pp. 2349-2353.

Tasso Miliotis, et al., "Capillary Liquid Chromatography Interfaced to Matrix-Assisted Laser Desorption/Ionization Time-of-Flight Mass Spectrometry Using an On-Line Coupled Piezoelectric Flow-Through Microdispenser," J. Mass Spectrom., vol. 35, 2000, pp. 369-377.

Bradley J. Larson, et al., "Controlled Deposition of Picoliter Amounts of Fluid Using an Ultrasonically Driven Micropipette," Review of Scientific Instruments, vol. 75, No. 4, Apr. 2004, pp. 832-836.

T. Laurell, et al., "Design and Development of a Silicon Microfabricated Flow-Through Dispenser for On-Line Picolitre Sample Handling," J. Micromech. Microeng., vol. 9, 1999, pp. 369-376.

Bernd O. Keller, et al., "Detection of 25,000 Molecules of Substance P by MALDI-TOF Mass Spectrometry and Investigations into the Fundamental Limits of Detection in MALDI," J. Am. Soc. Mass Spectrom., vol. 12, 2001, pp. 1055-1063.

Priscilla Wilkins Stevens, et al., "Imaging and Analysis of Immobilized Particle Arrays," Analytical Chemistry, vol. 75, No. 5, Mar. 1, 2003, pp. 1147-1154.

Priscilla Wilkins Stevens, et al., "Immobilized Particle Arrays: Coalescence of Planar- and Suspension-Array Technologies," Analytical Chemistry, vol. 75, No. 5, Mar. 1, 2003, pp. 1141-1146.

Jan Axelsson, et al., "Improved Reproducibility and Increased Signal Intensity in Matrix-Assisted Laser Desorption/Ionization as a Result of Electospray Sample Preparation," Rapid Communications in Mass Spectrometry, vol. 11, 1997, pp. 209-213.

Ole Vorm, et al., "Improved Resolution and Very High Sensitivity in MALDI TOF of Matrix Surfaces Made by Fast Evaporation," Analytical Chemistry, vol. 66, No. 19, Oct. 1, 1994, pp. 3281-3287.

Chung-Hsuan Winston Chen, et al., "Innovative DNA Microarray Hybridization Detection Technology," HGM 2002 Poster Abstracts: 12. New Technologies, Poster No. 516 (Abstract) 2002.

Daniel P. Little, et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, vol. 69, No. 22, Nov. 15, 1997, pp. 4540-4546.

Michael J. Bogan, et al., "MALDI-TOF-MS Analysis of Droplets Prepared in an Electrodynamic Balance: 'Wall-Less' Sample Preparation," Analytical Chemistry, vol. 74, No. 3, Feb. 1, 2002, pp. 489-496.

Patrik Onnerfjord, "Mass Identity of Biomolecules by MALDI-TOF MS," pp. 1-12.

John A. Castro, et al., "Matrix-Assisted Laser Desorption/Ionization of High-Mass Molecules by Fourier-Transform Mass Spectrometry," Radip Communications in Mass Spectrometry, vol. 6, 1992, pp. 239-241.

Bashir A. Mansoori, et al., "Matrix-Assisted Laser Desorption/Ionization of Size- and Composition-Selected Aerosol Particles," Analytical Chemistry, vol. 68, No. 20, Oct. 15, 1996, pp. 3595-3601.

Stanislav S. Rubakhin, et al., "Measuring the Peptides in Individual Organelles with Mass Spectrometry," Nature Biotechnology, vol. 18, Feb. 2000, pp. 172-175.

Osamu Yogi, et al., "On-Demand Droplet Spotter for Preparing Pico- to Femtoliter Droplets on Surfaces," Analytical Chemistry, vol. 73, No. 8, Apr. 15, 2001, pp. 1896-1902.

Patrik Onnerfjord, et al., "Picoliter Sample Preparation in MALDI-TOF MS Using a Micromachined Silicon Flow-Through Dispenser," Analytical Chemistry, vol. 70, No. 22, Nov. 15, 1998, pp. 4755-4760.

E. Peter Maziarz, et al., "Post-Gel Permeation Chromatography Polymer Blend Analysis From a Raster-Deposited Matrix-Assisted Laser Desorption/Ionization Target," Rapid Communications in Mass Spectrometry, Letters to the Editor, vol. 17, 2003, pp. 2450-2454.

Zheng Ouyang, et al., "Preparing Protein Microarrays by Soft-Landing of Mass-Selected Ions," Science, vol. 301, Sep. 5, 2003, pp. 1351-1354.

Dhaval N. Gosalia, et al., "Printing Chemical Libraries on Microarrays for Fluid Phase Nanoliter Reactions," PNAS, vol. 100, No. 15, Jul. 22, 2003, pp. 8721-8726.

Tasso Millotis, et al., "Ready-Made Matrix-Assisted Laser Desorption/Ionization Target Plates Coated with Thin Matrix Layer for Automated Sample Deposition in High-Density Array Format," Rapid Communications in Mass Spectrometry, vol. 16, 2002, pp. 117-126.

Eckhard Nordhoff, et al., "Sample Preparation Protocols for MALDI-MS of Peptides and Oligonucleotides Using Prestructured Sample Supports," International Journal of Mass Spectrometry, vol. 226, 2003, pp. 163-180.

Johan Gobom, et al., "Sample Purification and Preparation Technique Based on Nano-Scale Reversed-Phase Columns for the Sensitive Analysis of Complex Peptide Mixtures by Matrix-Assisted Laser Desorption/Ionization Mass Spectrometry," J. Mass Spectrom., vol. 34, 1999, pp. 105-116.

W. Travis Berggren, et al., "Single-Pulse Nanoelectrospray Ionization," Analytical Chemistry, vol. 74, No. 14, Jul. 15, 2002, pp. 3443-3448.

Scott D. Hanton, et al., "Investigations of Electrospray Sample Deposition for Polymer MALDI Mass Spectrometry," J. Am. Soc. Mass Spectrom., vol. 15, 2004, pp. 168-179.

David Ericsson, et al., "Ultrasensitive MALDI-TOF-MS with Picoliter Volume Sample Handling," Mass Spectrometry and Hyphenated Techniques in Nueropeptide Research, 2002, pp. 235-255.

* cited by examiner

DEPOSITION OF SAMPLES AND SAMPLE MATRIX FOR ENHANCING THE SENSITIVITY OF MATRIX ASSISTED LASER DESORPTION/IONIZATION MASS SPECTROMETRY

BACKGROUND

Matrix-assisted laser desorption/ionization (MALDI) mass spectrometry has proven to be a useful analytical tool in the fields of proteomics and genomics. In these fields, MALDI has been used for protein identification and characterization, peptide fingerprinting, and DNA sequencing. Samples that are commonly analyzed using MALDI include peptides, proteins, polymers, oligonucleotides, oligosaccharides, tissue samples, and drugs.

Unfortunately, broader applications for MALDI mass spectrometry have been limited by the fact that detection sensitivity is restricted by sample handling and preparation techniques. Many of these limitations stem from the fact that current techniques for preparing sample spots on MALDI targets produce relatively large inhomogeneous sample spots. These large spots require a considerable amount of sample and often waste sample because only a small fraction of the sample spot is actually irradiated for ion generation during MALDI mass spectrometry. In addition, inhomogeneous sample spots may result in highly variable ion signals produced from a single sample spot.

The dried-droplet method is a well-known technique for creating sample spots on a MALDI target. In the dried-droplet method, a mixture of analyte and matrix solution is deposited in small volumes onto a MALDI target where a sample spot is left to dry and crystallize within a few minutes. The resulting sample spots are inhomogeneous spots having a spot size of about 4–5 mm$^2$. Another technique commonly used to deposit sample spots on a MALDI target is electrospray deposition. In this technique, a small amount of matrix-analyte mixture is electrosprayed from a stainless-steel or glass capillary onto a grounded metal sample plate mounted a short distance away from the tip of the capillary. The spot size of sample spots deposited using electrospray deposition is typically about 100 μm or larger in diameter. Quill pen dispensation is another method for depositing sample spots on a MALDI target. Although quill pens have been used to produce sample spots having diameters as small as 75 micrometers using aqueous solutions, these pens are poorly suited for depositing small sample spots for MALDI applications because the saturated crystallized solutions used as matrix materials on a MALDI target tend to crystallize within and clog the quill pen tips.

More recently, attempts have been made to produce MALDI targets having small sample spots using piezoelectric microdispensers. Miliotis et al. have reported a method for producing MALDI targets using a piezoelectric microdispenser to apply sample spots to the target. *Rapid Commun. Mass Spectrom.*, 2002, Vol. 16, pp. 117–126. However, even the reduced sample spot sizes achieved with these devices are typically at least 100 μm in diameter, and typically much larger. These larger spot sizes may be attributed to the mechanism of operation of the piezoelectric microdispensers, which relies on a cylindrical piezoelectric element surrounding a capillary to compress and expand the capillary, squeezing fluid from the capillary.

Meier et al. have reported the formation of a MALDI target using ink jet printing technology to deposit sample spots. *Rapid Commun. Mass Spectrom.*, 2003, Vol. 17, pp. 2349–2353. The reported spot diameter for the ink jet printed sample spots was about 180–200 micrometers. However, due to problems with ink jet clogging, common MALDI solvents such as tetrahydrofuran and chloroform could not be used.

Thus, a need exists for a MALDI target composed of small homogeneous sample spots and methods for producing the same.

SUMMARY OF THE INVENTION

This invention relates to a layered MALDI target having at least one sample spot. In some instances the at least one sample spot will have a small diameter. For example, the MALDI target may have at least one sample spot with a diameter of no more that about 50 micrometers. The sample spot may include a layer of analyte disposed on a MALDI target substrate with a layer of matrix material disposed over the analyte or a layer of matrix material disposed on a MALDI target with a layer of analyte disposed over the matrix material. The at least one sample spot is deposited using ultrasonic deposition from a nozzle. During ultrasonic deposition, a nozzle (e.g., a capillary) is vibrated at ultrasonic frequencies to cause fluid in the nozzle (e.g., analyte solutions or matrix solutions) to be deposited from the nozzle tip onto a target substrate. This mechanism is capable of providing smaller sample spot sizes than conventional piezoelectric-based capillaries, which use pressure to squeeze fluid out of a nozzle tip by contracting and expanding the nozzle using a cylindrical piezoelectric element surrounding the nozzle.

The MALDI targets in accordance with the invention having very small sample spots disposed thereon have several advantages over other MALDI targets presently available. The small sample spots result in better signal-to-noise ratios, require less analyte, and do not waste analyte. Small spot sizes also allow for higher density of analyte samples on a single substrate. As a result, the MALDI targets provided herein make quick, automated, high-throughput MALDI analysis possible.

The sample spots may be deposited on a MALDI target substrate using the ultrasonically actuated microplotter described in U.S. Patent Application Publication No. 2004/0071601, the entire disclosure of which is incorporated herein by reference. Briefly, a sample spot may be deposited on a MALDI target substrate using the ultrasonically actuated microplotter by first applying a layer of analyte solution to the substrate surface and then applying a matrix solution over the analyte solution. The analyte solution is desirably applied to the target as one or more small spots with the matrix solution being applied in the form of spots laid down on top of the analyte spots. However, other constructions are possible. For example, the analyte may be laid down as one or more spots on the MALDI target substrate with the matrix solution laid down as a single stripe or sheet covering multiple spots. Alternatively, the analyte sample may be laid down on the MALDI target substrate as a stripe or a sheet and the matrix solution may be laid down as one or more spots over the analyte sample. In other constructions, the matrix solution may be applied (e.g., as spots, stripes or a sheet) to the target substrate first, then covered with analyte solution (e.g., as spots, stripes, or a sheet).

Generally a method for producing a sample spot on a MALDI target may be carried out according to the following procedure. A nozzle which circumferentially surrounds an interior passage extending between a dispensing end and an opposite end is provided. A first fluid which may be either an analyte solution or a matrix material solution is introduced into the interior passage of the nozzle. The nozzle is then situated above a MALDI target substrate and actuated at a portion of its circumference at a frequency sufficient to deposit the first fluid from the dispensing end of the nozzle onto the substrate. A second fluid which comprises either analyte solution or MALDI matrix solution, whichever was not introduced as the first fluid, is then introduced into the interior passage of the nozzle. The nozzle is then situated above the first fluid dispensed onto the MALDI target substrate and ultrasonically actuated at a portion of its circumference at a frequency sufficient to deposit the second fluid from the dispensing end of the nozzle and onto the first fluid which was previously dispensed onto the substrate. (When the analyte solution is deposited first, additional time may be allowed to pass before applying the matrix material to the substrate to allow the solvent in the spots of analyte solution on the target substrate to evaporate.) Any fluid remaining in the nozzle after either fluid dispensation step may be disposed of by reactivating the ultrasonic actuator to dispense the remaining fluid into a suitable receptacle. The nozzle then may be rinsed by drawing a rinsing fluid into the nozzle and reactivating the ultrasonic actuator to dispense the rinsing fluid into a suitable receptacle.

Suitable analyte materials used in the production of the MALDI targets provided herein include biomolecules, polymers, small molecules, and complex mixtures, such as tissue samples.

Further objects, features, and advantages of the invention will be apparent from the following detailed description when taken in conjunction with the accompanying drawings.

DETAILED DESCRIPTION

The present invention relates to MALDI targets having very small sample spots deposited thereon and methods for making such MALDI targets. The MALDI targets in accordance with the invention require only a small amount of sample per spot and allow for a high density of sample spots on a single target substrate surface. As a result, the MALDI targets provide quick, automated, high-throughput, high-sensitivity MALDI analysis of samples. The MALDI targets preferably include one or more sample spots having a diameter of no more than about 70 micrometers, and most preferably no more than about 50 micrometers, disposed on a MALDI target substrate. Each sample spot is a layered spot including a layer of analyte and a layer of crystallized matrix material. The layered MALDI sample spots are produced in a stepwise fashion using an ultrasonically actuated fluid dispensation apparatus.

Figure 1:
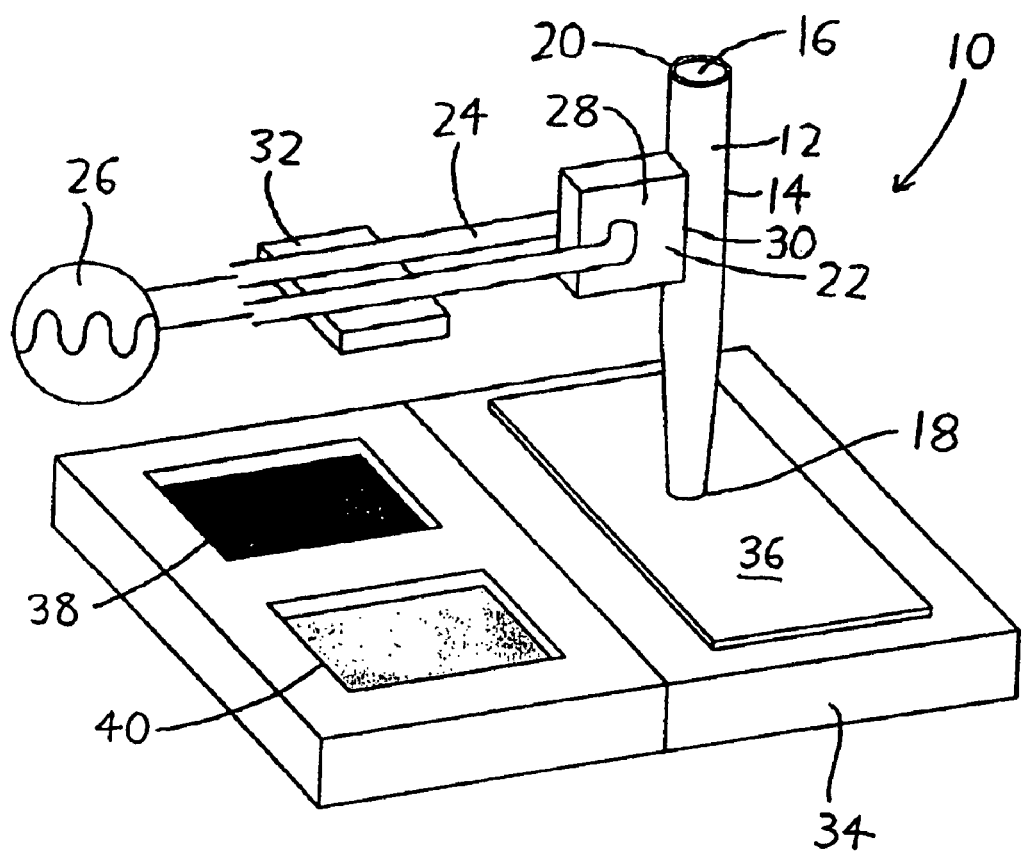
FIG. 1 is a perspective view of an exemplary version of a fluid dispensation apparatus that may be used to produce MALDI targets with small spot sizes.

FIG. 1 shows a diagram of an ultrasonically actuated fluid dispensation apparatus 10 for producing MALDI targets with small spot sizes. A more detailed description of the apparatus may be found in U.S. Patent Application Publication No. 2004/0071601 which is incorporated herein by reference. The apparatus 10 includes an elongated nozzle 12 which is defined by a nozzle outer surface 14 and a nozzle interior passage 16 extending between a nozzle dispensing end 18 and an opposite end 20. The dispensing end 18 is desirably narrowed compared to the opposite end 20 such that the cross sectional area of the interior passage 16 is smaller at the dispensing end 18 than at the opposite end 20. The interior passage 16 of the nozzle may have a very small diameter. For example, some nozzles, including some glass nozzles, may be made with an interior passage or bore of between 250 nm and 100 µm in diameter, although nozzles with interior passage diameter falling outside of these ranges may also be employed.

The nozzle may be filled by drawing fluids into the nozzle 12 using capillary action when the dispensing end 18 is inserted into a fluid supply. In such embodiments, the nozzle's opposite end 20 is desirably left open to the atmosphere so that the intake of fluid into nozzle interior passage 16 will not be hindered by air pressure within the interior passage 16 of the nozzle 12 at the opposite end 20. While the apparatus is well suited to a dip-and-dispense methodology (wherein the nozzle 12 is charged by dipping it in an appropriate well), the nozzle 12 may also be charged via a fluid supply connected to its opposite end 20 (as by a flexible or rigid fluid supply line). If necessary, damping caused by the fluid supply line may be compensated for by modification of the frequency and voltage ranges used to operate the apparatus.

An ultrasonic actuator 22 is coupled to a portion of the circumference of the nozzle's outer surface 14. In one embodiment, the ultrasonic actuator 22 is a diced piece of piezoelectric material bonded to the nozzle's outer surface 14. Unlike conventional piezoelectric dispensing devices, the nozzle 12 in the device of FIG. 1 does not operate via a peristaltic-type constriction and expansion of the diameter of the nozzle 12.

Conducting leads 24 attached to the ultrasonic actuator 22 allow for the expansion and contraction of the ultrasonic actuator 22 when appropriately powered by a signal generator such as a standard oscillator/function generator capable of supplying power with sinusoidal or similar waveforms at ultrasonic frequencies.

The nozzle 12 may be mounted on a positioning stage 32 to allow a user to position the nozzle dispensing end 18 at a desired location. The positioning stage 32 may take the form of any number of positioning stages known in the art.

A substrate mount 34 suitable for receiving a MALDI target substrate 36, such as a stainless-steel substrate with a top surface, is disposed below the nozzle dispensing end 18. The substrate mount 34 may itself be mounted on a positioning stage to allow the user to position the MALDI target substrate 36 relative to the dispensing nozzle 12. A fluid supply well 38 for the matrix material and a separate fluid supply well for an analyte solution 40 are desirably positioned in a location accessible to the nozzle dispensing end 18 such that the nozzle dispensing end 18 may be inserted into the fluid supply wells allowing the nozzle 12 to be filled with fluid via capillary action. The fluid supply wells may themselves optionally be mounted to a positioning stage. An additional fluid supply well (not shown) containing a rinsing fluid, such as de-ionized water, for cleaning the nozzle 12 and its interior passage 18 may also be provided.

A MALDI target may be prepared using the ultrasonically actuated fluid dispensation apparatus according to the following procedure. The nozzle 12 is inserted into a first fluid supply well 38 containing an analyte solution, at least a portion of which is drawn into the interior passage 16 of the nozzle. For example, the solution may be drawn into the interior passage via capillary action. The dispensing end 18 of the nozzle 12 is then positioned over a desired location on the surface of the substrate 36 by appropriate positioning of the nozzle 12 and/or the substrate mount 34. The signal generator 26 is then activated to send an oscillating voltage signal via conducting leads 24 to the piezoelectric actuator 22, causing it to vibrate at ultrasonic frequencies for a selected period of time, causing the fluid in the nozzle to be dispensed onto the MALDI target substrate 36 as a small spot of fluid. The size of the resulting spot depends on the amount of fluid dispensed from the nozzle 12 (which depends in part on how hydrophilic the nozzle 12 is, as well as the frequency, amplitude, and time duration of ultrasonic actuation), the distance between the nozzle dispensing end 18 and the surface of the MALDI target substrate 36, and the relative properties of the fluid and the substrate 36 (e.g., the polarity of deposited fluid relative to the polarity of the material of the substrate 36, the viscosity of the fluid and the wettability of the substrate surface or previously deposited layer on which the material is deposited). Once the first spot is deposited onto the MALDI target substrate 36, a MALDI matrix solution may be introduced into the nozzle 12 and the nozzle 12 may be repositioned over the MALDI target substrate 36 and a second spot deposited in the same manner as the first. This process may be repeated until the desired number of sample spots has been deposited onto the MALDI target substrate 36. Alternatively, all of the analyte spots may be deposited is a first step and all of the matrix spots deposited over the analyte spots in a second step.

In an alternative embodiment, the ultrasonic actuator 22 is excited continuously while the MALDI target substrate 36 (or the nozzle) is moved from a first position to a second position such that a strip of analyte is deposited onto the MALDI target substrate 36 rather than a spot. The nozzle 12 may then be repositioned over the first fluid supply well 38 and the ultrasonic actuator 22 reactivated to dispense any remaining analyte solution from the interior passage 16 of the nozzle. Next, the nozzle 12 may be positioned over a rinsing fluid supply well (not shown), and inserted into the supply well such that rinsing fluid is drawn into the interior passage 16 of the nozzle 12 via capillary action. The nozzle may then be lifted from the rinsing fluid supply well and the ultrasonic actuator 22 may be activated to dispense the rinsing solution.

After rinsing, the nozzle 12 may then be inserted into a fluid supply well 40 containing a solution of matrix material. At least a portion of the solution of matrix material is then drawn into the nozzle 12. For example, the solution may be drawn into the nozzle via capillary action. The nozzle is then positioned over the target substrate 36 which has a series of spots or a strip of analyte previously deposited on the MALDI target substrate 36, and the actuator 22 is activated to dispense matrix material over the spots or strip of analyte in the manner as described above. This process is repeated until each of the analyte spots or analyte strips is coated with corresponding spots or strips of MALDI matrix material.

Sufficient time may be allowed to pass before applying the matrix material to the substrate to allow the solvent in the spots of analyte solution on the target substrate to evaporate.

Alternatively, the matrix material may be applied to the target substrate first, followed by deposition of the analyte. This may be accomplished by modifying the above-described procedures to dispense the matrix solution prior to the analyte solution.

As noted above, the size of the deposited spots will be a function of the frequency, amplitude, and time duration of ultrasonic activation, and these parameters, in turn, may vary due to differences in viscosity and wetting properties of the different solutions being dispensed. The optimal frequency and power level of activation may vary over a wide range depending upon a number of factors including, but not limited to, the nature of the piezo material used and the size of the nozzle. By way of illustration only, in some instances the actuator may be activated at 300 to 800 kHz (e.g., in the range of 640 to 670 kHz) using 1 to 6 V (e.g., 1 to 2 V) peak-to-peak pulses applied for a duration of e.g., 100 to 1000 ms, preferably 400 to 500 ms, for the dispensation of analyte solution. The same parameters may be used to dispense matrix solution, although a somewhat higher voltage (e.g., 1 to 8 V) may be used. However, the invention is not limited to methods using these activation parameters.

In one embodiment, the sample spots are composed of a spot of analyte covered by a spot of matrix material, or a spot of matrix material covered by a spot of analyte. In this embodiment, the sample spot is the spot of analyte (or matrix material) plus the overlying spot of matrix material (or analyte). In another embodiment, the MALDI targets are produced by laying down one or more spots of analyte and covering the one or more spots of analyte with a strip or a sheet of matrix material or by laying down one or more spots of matrix material and covering them with a strip or sheet of analyte. In this embodiment, the sample spot is a spot of analyte (or matrix material) plus the matrix material (or analyte) that is disposed over that spot. In yet another embodiment, the MALDI targets are produced by laying down a strip or sheet of analyte material on a MALDI target substrate and depositing one or more spots of matrix material on the strip or sheet of analyte or by laying down a strip or sheet of matrix material and depositing one or more spots of analyte on the strip or sheet. In this embodiment, a sample spot is a spot of matrix material (or analyte) plus the analyte (or matrix) material disposed under the matrix material (or analyte) spot. In still another embodiment, the MALDI targets are produced by laying down strips of analyte material on a MALDI target substrate and depositing one or more orthogonal strips of matrix material over the strips of analyte material, or by laying down strips of matrix material and depositing one or more orthogonal strips of analyte material over the strips of matrix material. In this embodiment, sample spots are defined by the overlapping portions of the orthogonal strips.

Using an ultrasonically actuated microplotter of the type described above, very small sample spot sizes may be achieved. For example, in some embodiments, sample spot sizes of no more than about 50 micrometers in diameter are provided. This includes embodiments where the sample spot size is no more than about 40 micrometers in diameter, no more than about 30 micrometers in diameter, no more than about 25 micrometers in diameter, no more than about 20 micrometers in diameter, or even smaller. For example, in some embodiments, the size of the sample spot deposited using an ultrasonically actuated microplotter is between about 20 and 50 micrometers in diameter. This includes embodiments where the sample spots have diameters between about 20 and 30 micrometers. These spot sizes are on the order of the laser spot size used to irradiate the sample during MALDI analysis. Small spots eliminate the noise associated with larger, inhomogeneous spots, for which the signal varies depending on which portion of the spot is being irradiated by the laser. As a result, the small spot sizes result in uniform signal with very good signal-to-noise ratios as compared to the signal-to-noise ratios for larger sample spots. In addition, these small spot sizes make it possible to pack more sample spots onto a single MALDI target substrate. For example, in some embodiments, MALDI targets having a density of 400 spots/mm$^2$ may be produced. As a result, the MALDI targets provided herein allow for higher throughput and faster analysis of analytes than previously known MALDI targets.

The MALDI target substrate may typically have a flat surface and be made of a preferably non-reactive material such as stainless-steel. Other suitable substrate materials include, but are not limited to, other metals, polymer substrates, such as nitrocellulose, methyl cellulose, polyacrylamide, and poly(ethylene oxide), and glasses. A wide variety of analytes may be deposited on these targets for analysis. For example, synthetic polymers, biomolecules, small molecules, and complex mixtures such as tissue samples may be applied as analytes to the MALDI target substrates. More specifically, the analytes may include peptides, proteins, polymers, oligonucleotides, oligosaccharides, tissue samples, drugs, and combinations thereof. In some embodiments, all of the sample spots in an array of spots may contain a single type of analyte. Alternatively, different spots in an array of spots may include different analytes.

As described above, the analytes are initially applied to the MALDI target substrates as solutions of analyte in an appropriate solvent. Many analyte solvents are well known and commercially available. These include, but are not limited to, chloroform, acetonitrile, methanol, ethanol, acetophenone, anisole, toluene, methylbenzoate, isopropanol, and dichloromethane. Although the concentration of the analyte in the solvent may vary, in some embodiments the concentration of analyte in the solvent is desirably about 1 mM to 200 mM.

The matrix materials are applied in the form of a matrix material solution. These solutions are saturated or near saturated solutions of an organic compound that crystallizes into a matrix to facilitate desorption and ionization of analyte compounds in a sample spot. Many matrix materials are well known and commercially available. These include, but are not limited to, dithranol, nicotinic acid (NA), glycerol, sinapinic acid (SA), ferulic acid (FA), caffeic acid (CA), succinic acid (SA), 2,5-dihydroxy benzoic acid (2,5-DHB), α-cyano-4-hydroxy cinnamic acid (α-CHCA), 3-hydroxypicolinic acid (3-HPA), 2-(4-hydroxyphenylazo)-benzoic acid (HABA), 2,4,6-trihydroxy-acetophenone (THAP), 3-amino-4-hydroxy benzoic acid (3,4-AHB), 5-methoxysalicylic acid (MSA), 1-hydroxy isoquinoline (HIC), 2,6-dihydroxyacetophenone (DHAP), 4-hydroxy-3-methoxyphenylpyruvic acid (HMPPA), indole-3-pyruvic acid (IPA), and harmaline, 3-aminoquinilone (3-AQ).

The solvents used in the matrix material solutions may be the same as those solvents used to dissolve the analytes in the analyte solutions discussed above. Although the concentration of the matrix in the solvent may vary, in some embodiments the concentration of the matrix in the solvent will be about 10 to 60 wt. %.

EXAMPLES

Example 1

Spot Size Analysis

Figure 2:
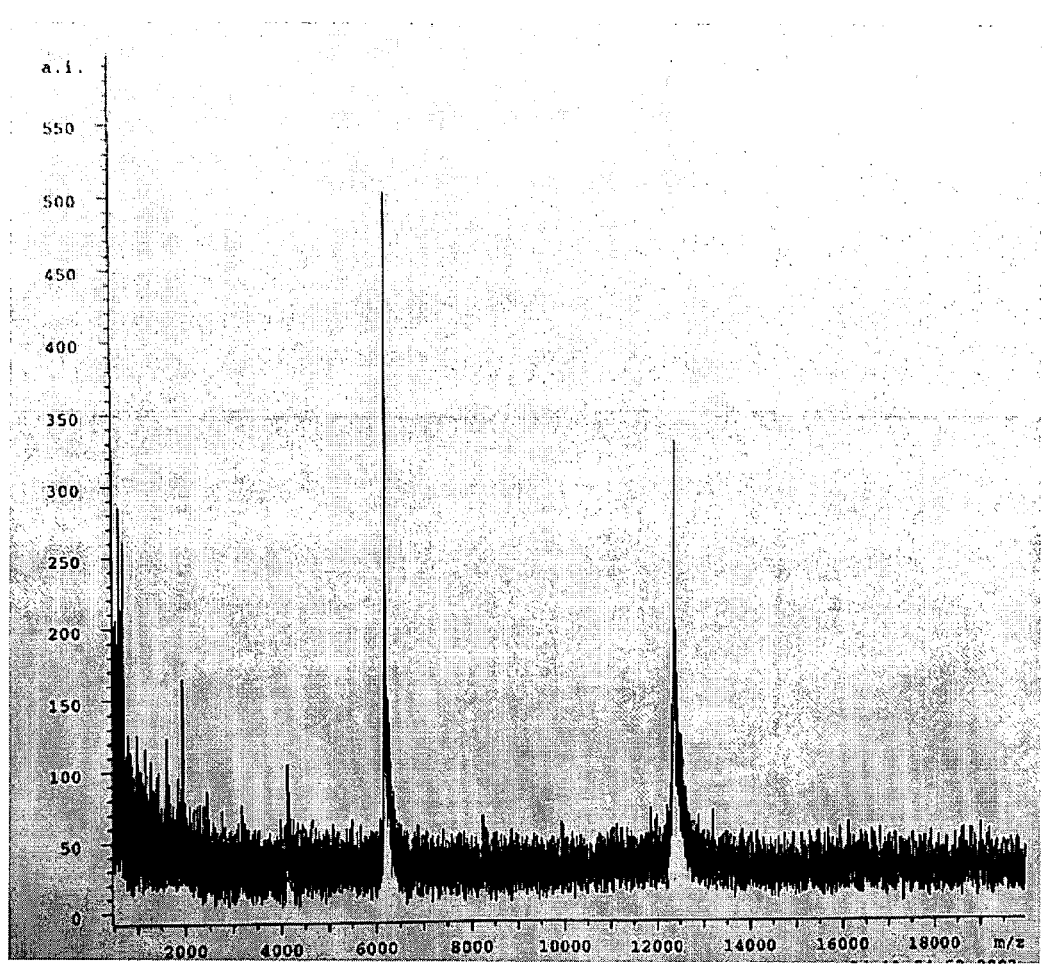
FIG. 2 shows the MALDI spectrum for a 70 µm sample spot formed of a layer of cytochrome C coated with a matrix of α-cyano-4-hydroxy cinnamic acid (α-CHCA).
Figure 3:
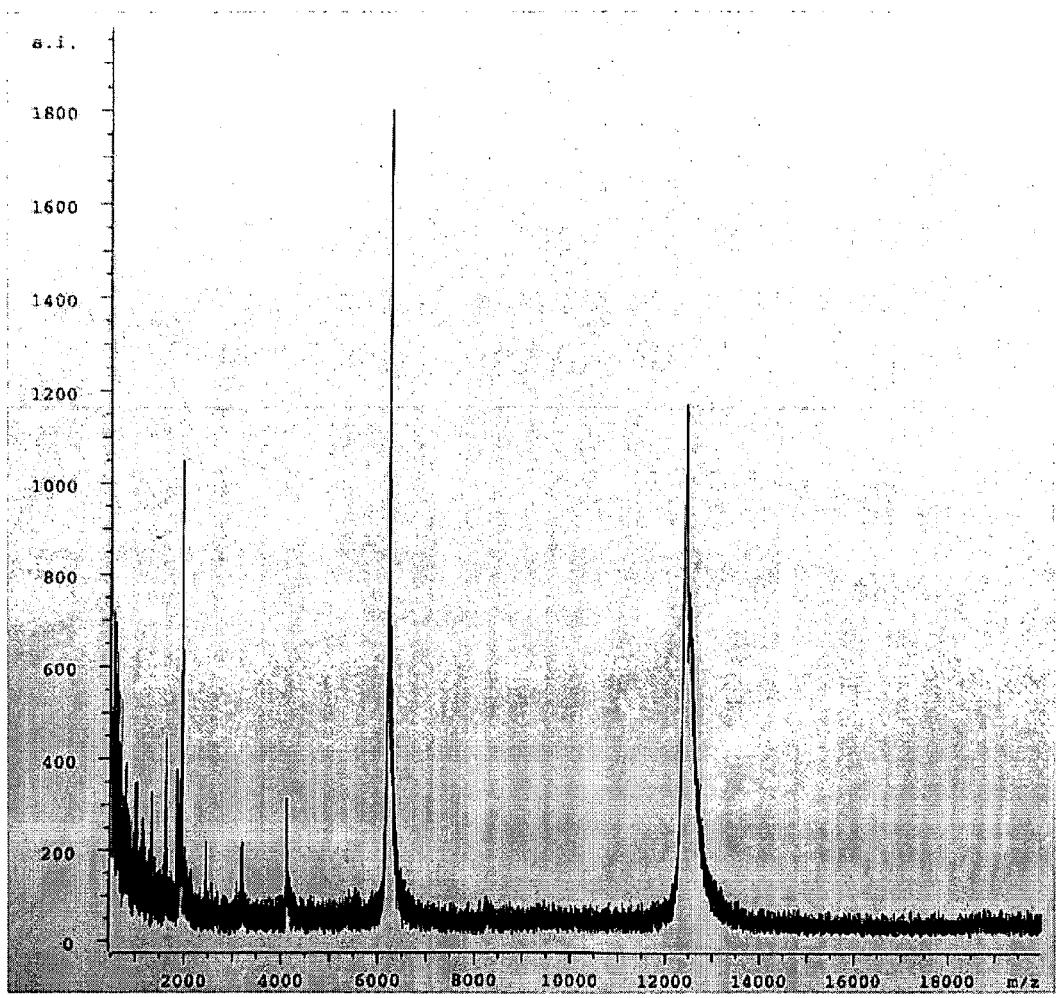
FIG. 3 shows the MALDI spectrum of a 20 µm sample spot formed of a layer of cytochrome C coated with a matrix of α-CHCA.

This Example demonstrates the effect of spot size on signal-to-noise ratio. A 10-mM solution of cytochrome C, with deionized (DI) water as solvent, was deposited on a stainless-steel MALDI target using the ultrasonically actuated microplotter described in U.S. Patent Application Publication No. 2004/0071601, then covered with a solution of α-CHCA matrix material dissolved in 30% DI water/70-% methanol solution. First, the dispenser was loaded with the cytochrome C solution and driven at 660 kHz and 1 V for a period of time sufficient to deposit approximately 75-μm-wide spots of the protein in a grid across the MALDI target. The dispenser was then cleaned with DI water and loaded with matrix solution. Two separate sets of matrix spots were deposited overlaying different portions of the spotted protein grid. One set of matrix spots was deposited at 660 kHz and 4 V to produce approximately 70-μm-wide spots, while the other set was deposited at 660 kHz and 2 V to produce approximately 20-μm-wide spots. After deposition, the MALDI target was loaded in a mass spectrometer. The laser was first targeted on a 70 μm spot and 50 shots were fired to gather a mass spectrum. The laser was then targeted on a 20 μm spot and 50 shots were fired to gather a second mass spectrum. Those spectra are shown in FIGS. 2 and 3, respectively. As can be seen from these figures, the spectrum from the 20-μm-wide spot exhibits a greatly enhanced signal-to-noise ratio as compared to the spectrum for the 70-μm-wide spot, resulting in an increased sensitivity of detection for the smaller spots.

Example 2

Deposition Pattern Analysis

Figure 4:
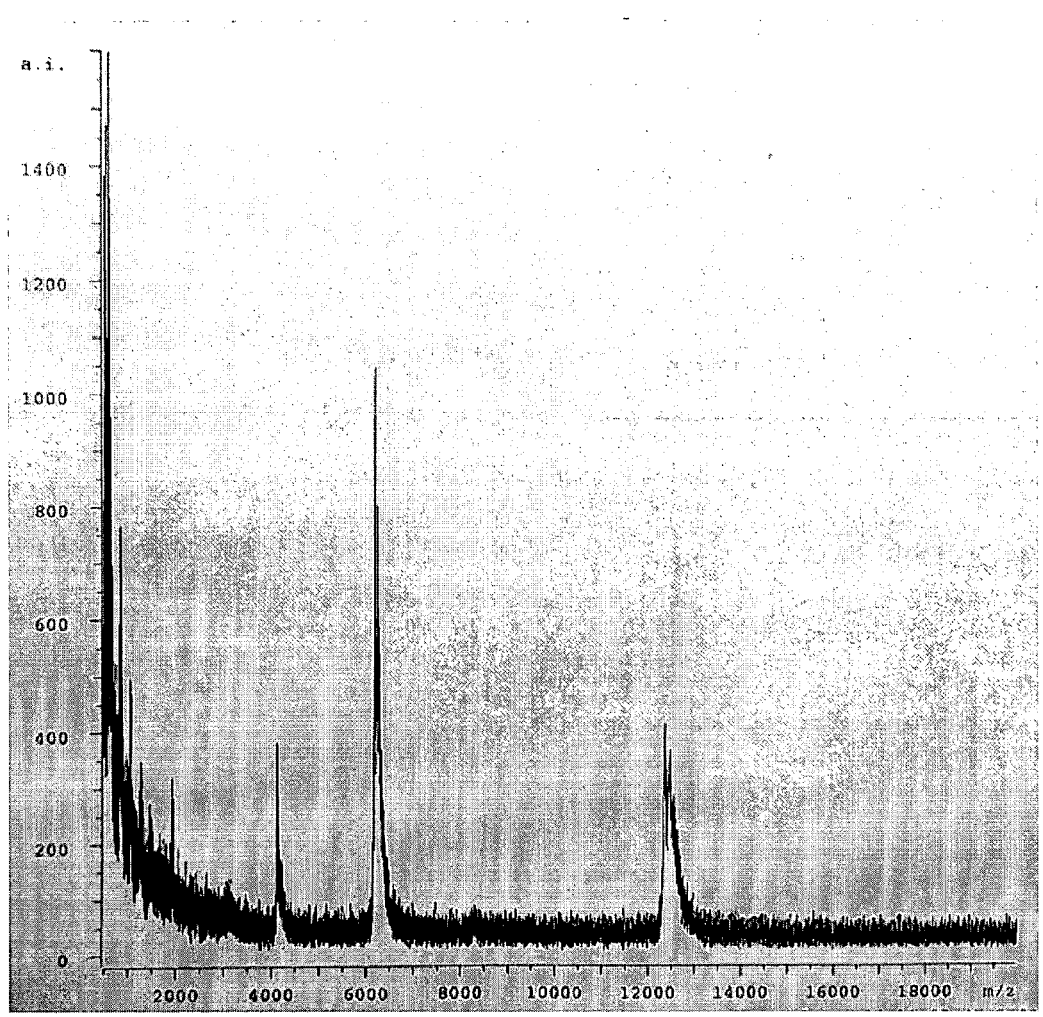
FIG. 4 shows the MALDI spectrum for a sample spot formed as a spot of cytochrome C coated with a strip of a α-CHCA matrix.
Figure 5:
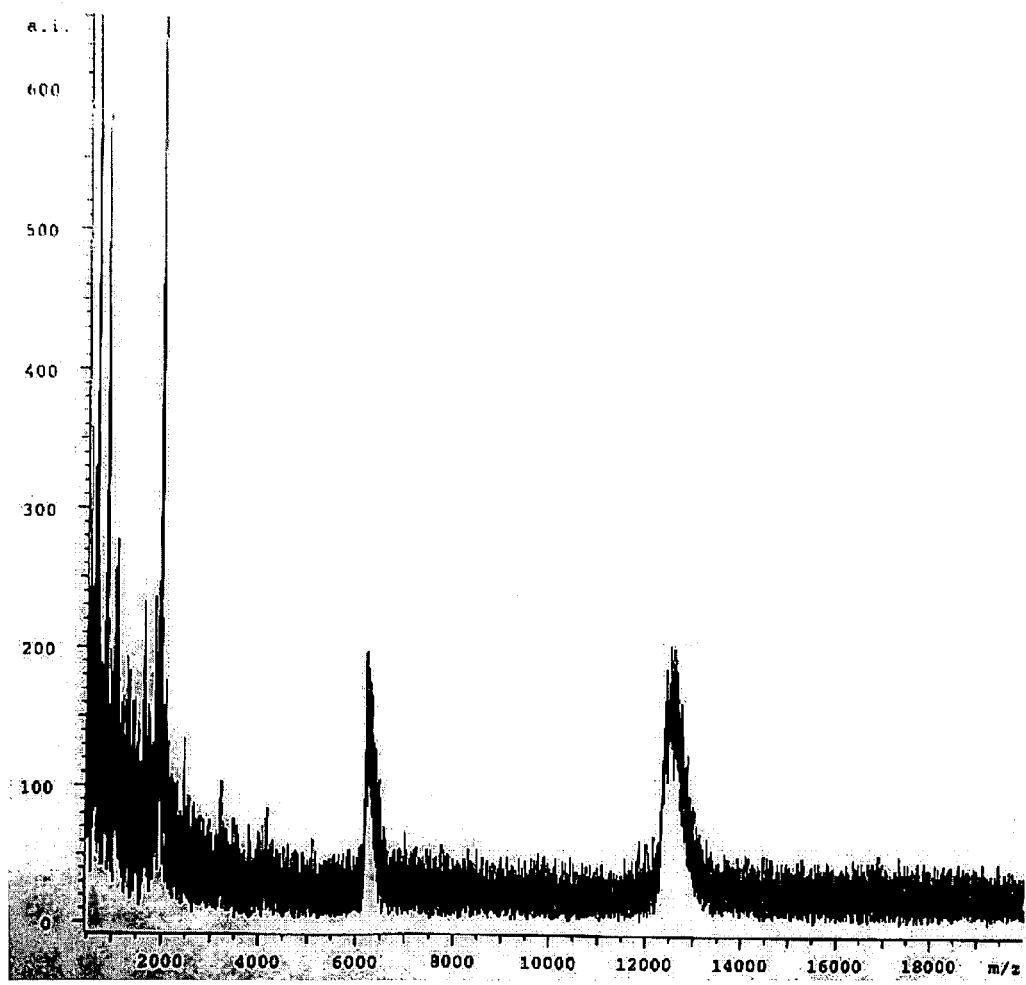
FIG. 5 shows the MALDI spectrum for a sample spot formed as a strip of cytochrome C having a spot of α-CHCA matrix deposited thereon.
Figure 6:
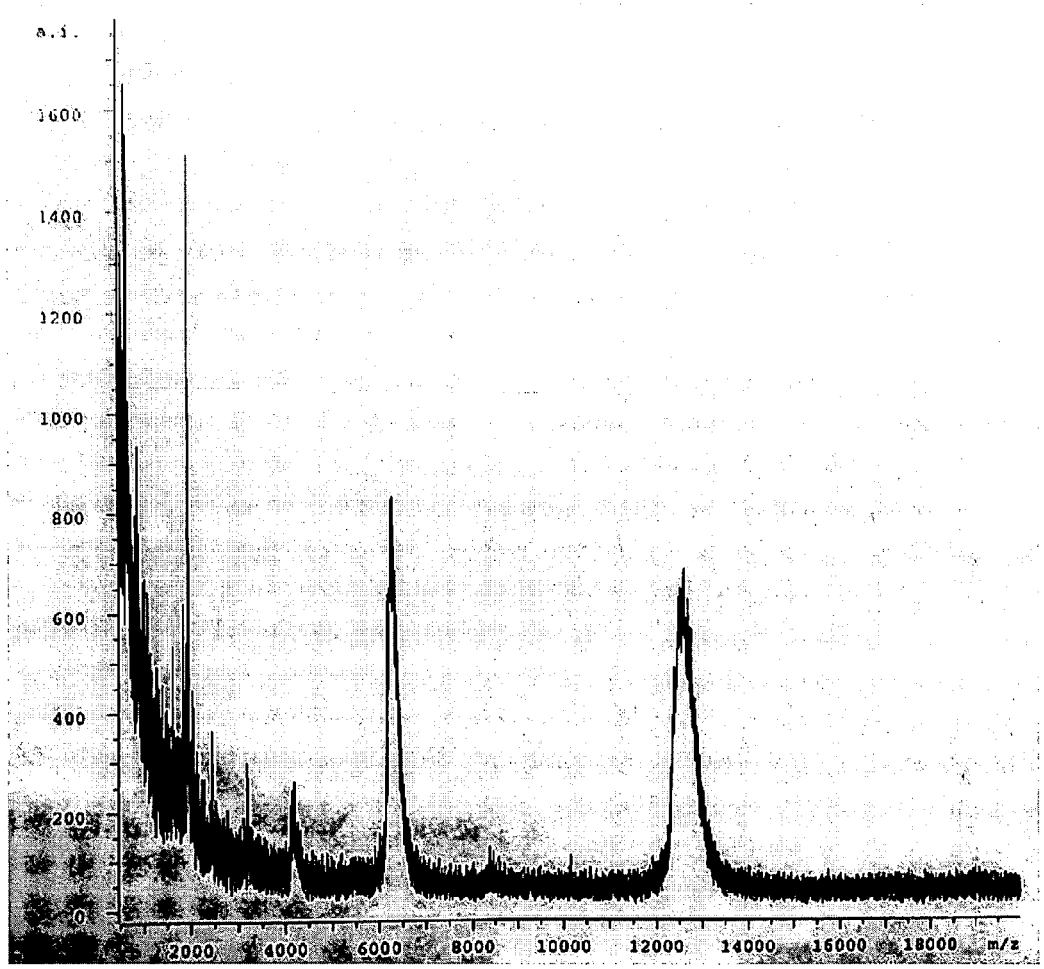
FIG. 6 shows the MALDI spectrum for a sample spot formed of a strip of cytochrome C having a strip of α-CHCA matrix deposited thereon.

A comparison between four different means of protein and matrix deposition was performed, using the same protein solution and matrix material described in Example 1. In addition to the previously described spots of matrix deposited on spots of protein, spots of matrix were deposited on a continuous coating of protein, a continuous coating of matrix was deposited on spots of protein, and a continuous coating of matrix was deposited on a continuous coating of protein. The continuous coatings were deposited by using the ultrasonically actuated microplotter to draw lines spaced so closely that an essentially uniform sheet of matrix or protein resulted. The lines were deposited at a speed of 1000 μm/s, a frequency of 660 kHz, and an amplitude of 1 V (for the protein) or 3V (for the matrix). Analysis was performed in the same mass spectrometer, with the same settings, used in Example 1. Mass spectra were obtained, as before, by targeting the laser onto the matrix spots, the analyte spots, and/or the intersection of the analyte and matrix strips. FIG. 4 shows the MALDI spectrum for the spot of cytochrome C coated with a strip of α-CHCA matrix. FIG. 5 shows the MALDI spectrum for the strip of cytochrome C having a spot of α-CHCA matrix deposited thereon, and FIG. 6 shows the MALDI spectrum for the strip of cytochrome C having a strip of α-CHCA matrix coated thereon. It can be seen that the uniformly coated areas have broader, less intense peaks in their spectra than the spotted matrix/spotted protein areas.

It is understood that the invention is not limited to the embodiments set forth herein for illustration, but embraces all such forms thereof that come with the scope of the following claims.

What is claimed is:

1. A method for producing a sample spot on a MALDI target substrate, the method comprising:
   (a) providing a dispenser having a nozzle which circumferentially surrounds an interior passage extending between a dispensing end and an opposite end;
   (b) introducing a first fluid into the interior passage of the nozzle, the first fluid comprising either an analyte solution or a MALDI matrix solution;
   (c) ultrasonically actuating the nozzle at a portion of its circumference at a frequency sufficient to deposit the first fluid from the dispensing end onto the substrate;
   (d) introducing a second fluid into the interior passage of the nozzle wherein the second fluid comprises either the analyte solution or the MALDI matrix solution, whichever was not introduced as the first fluid; and
   (e) ultrasonically actuating the nozzle at a portion of its circumference at a frequency sufficient to deposit the fluid from the dispensing end onto the first fluid on the substrate.

2. The method of claim 1 wherein the first fluid is deposited as one or more spots onto the substrate.

3. The method of claim 2 wherein the second fluid is deposited as one or more spots onto the first fluid.

4. The method of claim 2 wherein the second fluid is deposited as a strip onto the first fluid.

5. The method of claim 1 wherein the first fluid is deposited as a strip onto the substrate.

6. The method of claim 5 wherein the second fluid is deposited as one or more spots onto the first fluid.

7. The method of claim 5 wherein the second fluid is deposited as a strip onto the first fluid, the second fluid strip running orthogonal with respect to the first fluid strip.

8. The method of claim 2 wherein the one or more spots of the first fluid have a diameter of no more than about 50 micrometers.

9. The method of claim 2 wherein the one or more spots of the first fluid have a diameter of no more than about 30 micrometers.

10. The method of claim 3 wherein the one or more spots of the second fluid have a diameter of no more than about 50 micrometers.

11. The method of claim 3 wherein the one or more spots of the second fluid have a diameter of no more than about 30 micrometers.

12. The method of claim 6 wherein the one or more spots of the second fluid have a diameter of no more than about 50 micrometers.

13. The method of claim 6 wherein the one or more spots of the second fluid have a diameter of no more than about 30 micrometers.

14. The method of claim 1 wherein the analyte comprises a molecule selected from the group consisting of peptides, proteins, oligonucleotides, and oligosaccharides.

15. The method of claim 1 wherein the analyte comprises a synthetic polymer.

16. The method of claim 1 wherein the analyte comprises a tissue sample.

17. The method of claim 1 wherein the matrix material comprises a material selected from the group consisting of dithranol, nicotinic acid, glycerol, sinapinic acid, ferulic acid, caffeic acid, succinic acid, 2,5-dihydroxy benzoic acid, α-cyano-4-hydroxy cinnamic acid, 3-hydroxypicolinic acid, 2-(4-hydroxyphenylazo)-benzoic acid, 2,4,6-trihydroxy-acetophenone, 3-amino-4-hydroxy benzoic acid, 5-methoxysalicylic acid, 1-hydroxy isoquinoline, 2,6-dihydroxyacetophenone, 4-hydroxy-3-methoxyphenylpyruvic acid, indole-3-pyruvic acid (IPA), and harmaline, 3-aminoquinilone.

18. A MALDI target comprising multiple sample spots having diameters of no more than 50 micrometers disposed on a substrate, the target comprising spots of crystallized matrix material disposed on the substrate and a sheet comprising an analyte disposed over the spots of crystallized matrix material.

19. A MALDI target comprising multiple sample spots having diameters of no more than 50 micrometers disposed on a substrate, the target comprising one or more strips comprising an analyte disposed over the substrate and one or more strips of crystallized matrix material disposed over the substrate; wherein the sample spots are defined by overlapping portions of the strips comprising the analyte and the strips of crystallized matrix material.

20. A MALDI target comprising multiple sample spots having diameters of no more than 50 micrometers disposed on a substrate, the target comprising a sheet comprising an analyte disposed on the substrate and spots of crystallized matrix material disposed on the sheet comprising the analyte.

* * * * *